Figure 3:
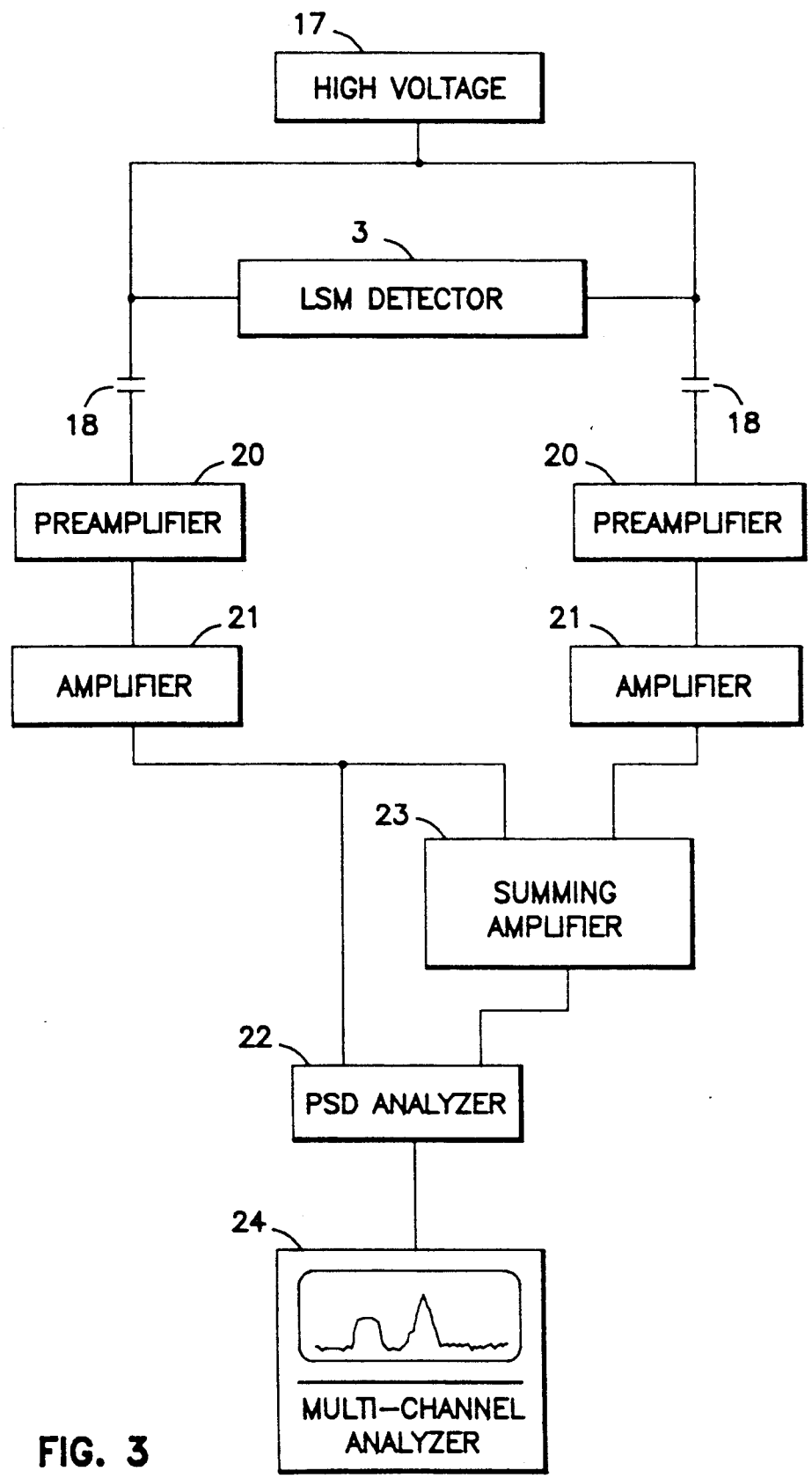

United States Patent [19]

Ritala et al.

[11] Patent Number: 5,025,154
[45] Date of Patent: Jun. 18, 1991

[54] PROCEDURE AND MEANS FOR MEASURING PAPER FORMATION

[75] Inventors: Risto Ritala, Helsinki; Mikko Laakso; Jari Koponen, both of Espoo, Finland

[73] Assignee: Kagaani Elektroniikka OY, Kajaani, Finland

[21] Appl. No.: 430,670

[22] Filed: Nov. 2, 1989

[30] Foreign Application Priority Data

Nov. 3, 1988 [FI] Finland .................................. 885067

[51] Int. Cl.$^5$ ............................................. G01N 23/16
[52] U.S. Cl. .................................. 250/308; 250/359.1; 250/374
[58] Field of Search .................. 250/308, 358.1, 359.1, 250/374, 385.1

[56] References Cited

U.S. PATENT DOCUMENTS 3,016,460 1/1962 Andresen ............................ 250/308
3,489,901 1/1970 Brown .................................. 250/308

FOREIGN PATENT DOCUMENTS 1179406 1/1970 United Kingdom ................. 250/374

Primary Examiner—Carolyn E. Fields
Attorney, Agent, or Firm—Merchant & Gould Smith, Edell, Welter & Schmidt

[57] ABSTRACT

A procedure for measuring the formation of paper, wherein through a paper sample is passed radiation and the radiation that has passed through the paper is observed with a $\beta$ radiation detector for establishing a spectrum characterizing the formation of the sample, for radiation source being used a liner $\beta$ radiation source, and the $\beta$ radiation that has passed through the sample being observed in one dimension with a position-sensitive wire chamber detector operating in limited streamer mode.

14 Claims, 2 Drawing Sheets

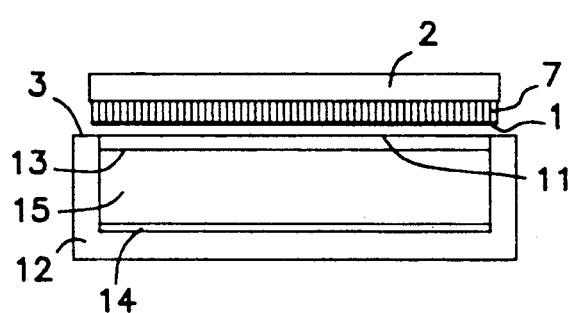
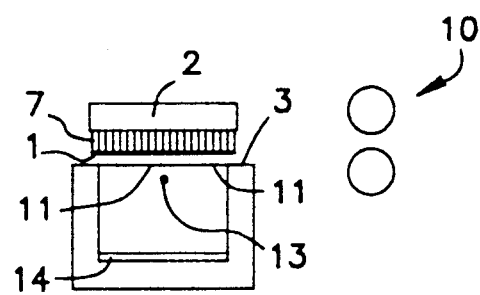
FIG. 1A  FIG. 1B
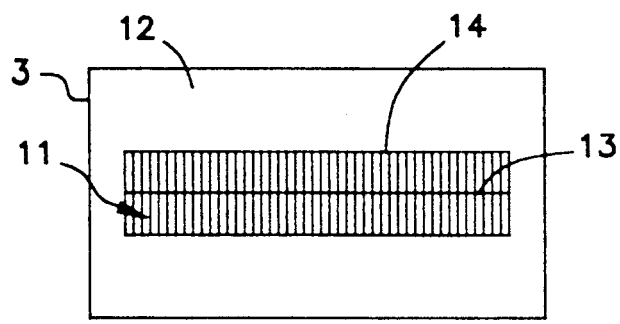
FIG. 1C
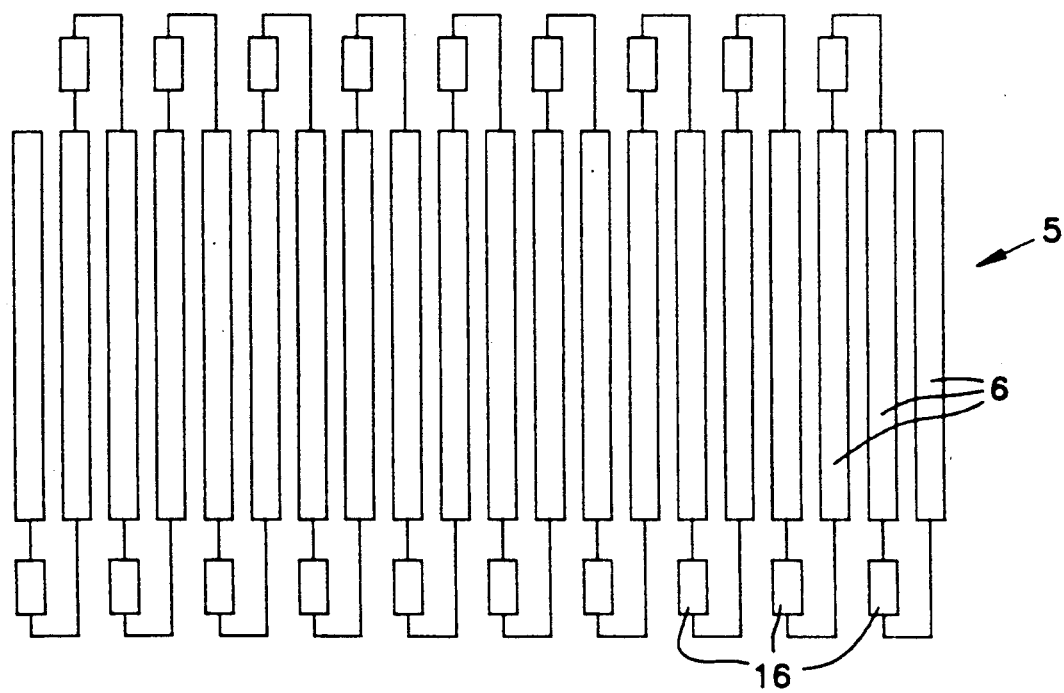
FIG. 2

PROCEDURE AND MEANS FOR MEASURING PAPER FORMATION

The present invention concerns a procedure for measuring the formation, that is the basis weight variations, of paper, in said procedure radiation being caused to pass through a paper sample and the radiation that has traversed the sample being observed with a radiation detector in order to form quantities characterizing the formation (or cloudiness) of the sample, in the first place a one-dimensional formation spectrum characterizing the floc distribution.

The invention further concerns a means for measuring paper formation, said means comprising a radiation source and a radiation detector for conducting radiation into the paper sample and observing the radiation that has passed through the sample, in order to establish a location dependence of the base mass variation characterizing the formation of the sample, and the power rate spectrum of these variations.

The formation of paper is understood to mean its small-scale (0.1 mm to 100 mm) base mass variation.

It is known in the art to measure formation of paper point by point, using a scintillation detector. It is further previously known to measure the formation of paper by the radiogram method. It is further known to measure the basis weight of the paper on a more extensive area, using an ionization chamber. In the measurements, one directs radiation through the sample, and said radiation is observed with a radiation detector in order to establish quantities characterizing the formation (with a scintillation detector, the scatter of basis weight; with the radiogram, scatter and floc size distribution; and with an ionization chamber, the mean of the basis weight). When visible light or other electromagnetic radiation is used, measurement of the formation of coated, filled or calender-processed paper causes problems because of the non-unambiguous dependence of transmittance to radiation and of basis weight. In particular when x-rays are used, sufficient resolution in basis weight is not achieved for establishing quantities characterizing the formation.

As the quality requirements imposed on paper continue to increase, measurement of paper formation has become increasingly important and desired in paper industry. It is not possible with existing procedures and means to measure, above all, the floc size distribution, i.e., the formation spectrum, rapidly, simply and reliably enough to make the procedure applicable in continuous off-line monitoring of formation.

The object of the present invention is to eliminate the drawbacks mentioned. The particular object of the invention is to provide a novel procedure for measuring formation which is well appropriate for use in efficient and rapid analysis of larger paper sample batches.

It is a further object of the invention to provide a novel procedure for establishing the power spectrum of variations in paper base mass in which procedure no operation is required which involves complex work steps, and several work steps.

It is a further object of the invention to provide a novel means for measuring paper formation which meets the requirements stated above, and which can be implemented in a simple way.

Regarding the features characterizing the invention, reference is made to the claims section.

The invention is based on the principle of using for radiation source a linear $\beta$ radiation source and observing the $\beta$ radiation passing through the paper, with a position-sensitive $\beta$ radiation detector, in other words: establishing the position dependence of basis weight characterizing the formation and the corresponding power spectrum, or the floc size distribution.

With $\beta$ radiation the advantage is gained that also measurement of the formation of ooated, filled or calender-treated paper can be reliably performed because both the fibre network and the pigments in the paper attenuate $\beta$ radiation in identical manner and the relationship between the intensity of $\beta$ radiation that has passed through a calendered sheet and the base mass is unambiguous.

When a linear $\beta$ radiation source is used for radiation source, the base mass of the paper can be measured on lineal areas of the paper, whereby the result of measurement will be in suitable form for establishing the one-dimensional power spectrum of the basis weight variations.

The procedure described in the invention can be implemented in such manner that no movable parts and no complicated work steps are required for establishing one formation spectrum, which are required when the formation spectrum is determined with the aid of radiograms.

In the procedure of the invention, the $\beta$ radiation generated by the radiation source is directed on a planar sample, preferably perpendicularly against the sample, with the radiation source, if linear, parallelling the sample. When the formation of a paper sample is being measured, the $\beta$ radiation passing through the sample is measured in the respective location on the other side of the paper, with a radiation detector. After the first measurement the paper may be moved with reference to the detector location just measured, e.g. in a direction at right angles, and the measurement may be repeated once or several times, at one or several lineal locations, for measuring the one-dimensional spectrum at several points of the sample.

A linear radiation source is understood to mean a radiation source comprising a linear element emitting $\beta$ rays, or a radiation source comprising a more extensive surface emitting $\beta$ rays plus elements, e.g. a slit, by the aid of which the $\beta$ rays are oriented into linear configuration.

The means of the invention comprises a $\beta$ radiation source and a position-sensitive wire chamber operating in so-called limited streamer mode (1) (LSM mode), serving as $\beta$ radiation detector; described in: M. Ellila et al. Limited Streamer Mode Detectors for Mass Production, Helsinki University, Report HU-SEFL-87-13, 1987.

Radiation source and detector have been disposed to be parallel, the radiation source to produce a radiation into the paper sample, and the detector to observe the $\beta$ radiation that has locally gone through the paper. The radiation detector is suitably connected to a signal analyzer for establishing the $\beta$ radiation intensity distribution characterizing the formation of the sample.

The $\beta$ radiation intensity distribution is measured by counting $\beta$ particles that have gone through a single paper sample and determining the location of each on the detector. The $\beta$ radiation detector comprises an anode wire and a cathode surface in the vicinity thereof. Between the anode wire and the cathode surface a high voltage is applied, by effect of which an electric field is present in the gas space, which has the direction from anode to cathode. The strength of the electric field is highest close to the anode wire, owing to the fact that the anode wire is thin, e.g. on the order of n ×101 to 102 μm (n = 1 to 10). A β particle directed through the measuring window into the gas space and through the paper sample will ionize atoms of the gas, producing free electrons and ions. By effect of the electric field the ions are driven towards the cathode, and the electrons towards the anode. The electric field is so strong in the vicinity of the anode that the electrons are multiplied and cause an electron avalanche by effect of the β particle, the current, or voltage pulse, caused by it being measured in the circuit. By selecting the high tension voltage and the gas mixture so as to make the detector operate in the so-called LSM mode, one obtains a highly intense discharge, which remains localized with sufficient accuracy.

The location of the current or voltage pulse, that is of the β particle, on the detector is determined e.g. by means of the charge division procedure. In the procedure, the detector cathode has been made e.g. of separate conductor elements, such as metal strips, between which resistors with identical resistance have been connected. When both ends of the cathode are connected to ground, the electric current resulting from the localized electron avalanches induced in proportion of the resistances visible at the ends. By measuring at both ends of the detector the charge contained in the current caused by the discharge, one is enabled to calculate the relative location of the discharge on the detector by the formula Xleft =Qright/(Qleft =Qright)     (I)

In practice, production of a signal proportional to the location is implemented by means of a separate electronic calculation system, e.g. as is presented below.

With a view to improving resolution, the paper sample has been advantageously arranged to be disposed in contact with the radiation source and with the corresponding radiation detector. Said arrangement then causes autocollimation, that is, the radiation detector measures mainly only that radiation which the radiation source emits at the location in question.

For improvement of resolution in the result of measurement, the β radiation produced by the radiation source may also be collimated with the aid of a collimator. The collimator comprises one or several absorbator plates in which has been formed a line of holes through which the radiation is conducted, for collimating the radiation.

When from a larger sample several formation spectra are determined, the means appropriately also comprises a feed means arranged to feed the paper sample through between the radiation source and the radiation detector and to measure the β radiation intensity distribution at various lineal locations on the sample, in accordance with the feeding of the sample.

The means of the invention may also comprise two or more linear radiation sources and corresponding radiation detectors, which have been disposed to measure the intensity distribution of the β radiation passing through the sample, simultaneously at a plurality of locations. The radiation sources are then, for instance, shaped like a straight line, and side by side and parallel. The radiation detectors may be connected e.g. in series. The measurement can be carried out e.g. with common charge division electronics or signal read-in electronics.

The invention is described, in the following, in detail with the aid of embodiment examples, referring to the enclosed drawing, wherein:

FIGS. 1A-C present a measuring geometry according to the invention as seen from the side, from above and from the end, and schematically depicted, FIG. 2 presents the cathode of the radiation detector of a means according to an embodiment of the invention, schematically depicted, and FIG. 3 presents the apparatus according to an embodiment of the invention, shown as a block diagram.

In FIGS. 1A-C is seen a linear or planar βradiation source 2, which has been disposed to emit βradiation onto a paper sample 1 that has been placed under the radiation source. The radiation source may also be provided with a collimator 7, which collimates the radiation emitted by the source. A β radiation detector 3 has been placed on the other side of the paper sample, with reference to the radiation source, that is, the sample is located between the radiation source and the detector, contacting the entrance window 11, transparent to β particles, of the detector. The collimator collimates the β radiation emitted from the radiation source 2 to become a linear beam.

The detector 3 comprises a gas-tight enclosure 12, an entrance window 11 joined with gas-tight sealing to said enclosure, an anode wire 13, and a cathode surface 14. The gas space 15 within the detector has been filled with a suitable gas mixture.

When the means depicted in FIGS. 1A-C is being used, the linear β radiation source 2 produces β radiation, which is collimated with the collimator 7 and passed through the paper sample 1 into the detector 3. Depending on the base mass of the paper, at different points of the sample different fractions of the β particles emitted by the β radiation source reach the detector at different points thereof. Thus the variations in base mass of the paper can be converted into variations of β radiation intensity on the surface of the detector, and the intensity variation is measured as a function of position. If desired, the sample 1 may be moved e.g. with the aid of a feed means 10, such as a roll conveyor or equivalent, for observing the βradiation transmitted by the sample at different points, e.g. at the locations of side-by-side, parallel lines with constant spacing.

In FIG. 2 is seen the resistive cathode 5 of the radiation detector, belonging to an embodiment of the invention. The cathode has been made of separate conductor elements 6, i.e., of metal strips, between which have been connected resistors 16 with identical resistances. When both ends of the cathode are connected to ground, the β particles arriving in the detector of FIG. 1 will induce localized electron avalanches, producing an electric current between the different ends of the cathode, in proportion to the resistors seen at the ends. It is possible by measuring the charge contained in the current produced by the discharge, at both ends of the detector, to calculate the location of the discharge on the detector accordingly as has been presented.

The arrangement serving to produce a signal proportional to the location of the electron avalanche, is to the location of the received β radiation, is presented in FIG. 3. The high voltage for the detector is generated with a high tension source 17. The charges at the ends 18,19 of the resistive cathode 5 of FIG. 2 are integrated with the aid of charge-sensitive preamplifiers 20, and the signals are further amplified with the aid of a linear amplifier 21. From one linear amplifier, the signal is carried directly to a division module 22, for which the other input is obtained by adding together the pulses from both linear amplifiers, using a summing module 23. The division module produces a pulse having a height proportional to the quotient of the inputs, i.e., according to formula (I) also to the location, counted from the end of the detector, of the discharge, that is, of the received β particle. Pulse height analysis of this signal, performed with a multichannel analyzer 24, will finally give directly the intensity distribution of the radiation, i.e., the βradiation spectrum on the surface of the detector.

The embodiment examples are only meant to illustrate the invention, and any embodiments of the invention may vary within the scope of the claims following below.

We claim:

1. A procedure for measuring paper formation, wherein radiation is made to pass through a paper sample and the radiation that has passed through the paper is observed with a β radiation detector, for establishing a spectrum characterizing the formation of the sample, characterized in that for radiation source is used a linear β radiation source and that the β radiation that has passed through the paper is observed in one dimension with a position-sensitive wire chamber detector operating in limited streamer mode.

2. Procedure according to claim 1, characterized in that the β radiation produced by the radiation source is collimated to become a linear beam, which is directed on the sample at right angles with respect to a plane in which the sample is positioned, with the radiation source paralleling the plane of the sample.

3. Procedure according to claim 1, characterized in that the sample is irradiated and radiation is measured with the radiation source substantially in contact with the sample and the sample substantially in contact with the detector.

4. Procedure according to any one of claims 1–3 characterized in that the β radiation spectrum that has passed through the sample is measured at a linear location, whereafter the paper is moved in a direction perpendicular against said linear location, and the measurement is repeated in order to measure a one-dimensional spectrum characterizing the formation of the paper, at several points of the sample.

5. A procedure according to claim 1, wherein the location of the β radiation is determined on the detector by means of the charge division procedure, wherein the detector includes a cathode that has been made of conductor elements between which resistors with identical resistance have been connected and the relative location of the discharge is determined by measuring at both ends of the detector the charge contained in the current caused by the discharge on the basis of the proportion of the resistances at the ends of the cathode.

6. An apparatus for measuring formation of paper (1), said apparatus comprising:
a radiation source (2) and a radiation detector (3) for imparting the radiation to a paper sample and observing the radiation that has passed through the sample, in order to establish a radiation intensity distribution characterizing the formation of the sample characterized in that the radiation source (2) is a linear β radiation source and that the detector (3) is a position-sensitive wire chamber detector operating in limited streamer mode.

7. An apparatus according to claim 6, characterized in that the β radiation detector (3) is connected to a signal analyzer (4).

8. An apparatus according to claim 6, characterized in that the wire chamber detector (3) comprises a resistive cathode (5) having separate conductor elements (6) which are connected to a signal analyzer (4).

9. An apparatus according to any of claims 1–5, characterized in that the apparatus comprises a collimator (7) which has been disposed to render the β radiation lineal.

10. An apparatus according to claim 9 characterized in that the collimator (7) is slit-like.

11. An apparatus according to claim 9, characterized in that the collimator (7) comprises at least one absorber plate in which has been provided a line of holes through which the β radiation is collimated.

12. An apparatus according to any one of claims 6–8, characterized in that the apparatus comprises a feed means (10) which has been disposed to feed the paper sample (1) through between the radiation source (2) and the radiation detector, and that the apparatus has been arranged to measure the βradiation spectrum at various points while the sample is being fed through between the radiation source and the detector.

13. An apparatus according to any one of claims 6–8, characterized in that the apparatus comprises at least two linear and parallel radiation sources (2) with their corresponding radiation detectors for determining formation simultaneously at several points of the sample.

14. An apparatus according to claim 6 wherein the position-sensitive wire chamber detector comprises a cathode made of conductor elements between which resistors with identical resistance have been connected and means for measuring at both ends of the detector the charge contained in the current caused by the discharge and means for calculating the relative location of the discharge on the cathode in proportion of the resistances at the ends of the cathode.

* * * * *

UNITED STATES PATENT AND TRADEMARK OFFICE
CERTIFICATE OF CORRECTION

PATENT NO. : 5,025,154

DATED : 18 June 1991

INVENTOR(S) : Risto Ritala et al.

It is certified that error appears in the above-identified patent and that said Letters Patent is hereby corrected as shown below:

On column 2, line 9 "ooated" should be --coated--.

On column 2, line 56 "a" should be --B--.

On column 3, lines 4 and 5 "101 to 102" should be --$10^1$ to $10^2$--.

On column 3, line 27 insert --by B particles becomes divided between the cathode ends-- after the word "induced".

On column 4, lines 12 and 13 "Bradiation" should be --B radiation--.

On column 4, line 43 "Bradiation" should be --B radiation--.

On column 4, line 61 insert --that-- after the word "avalanche".

On column 5, line 11 "Bradiation" should be --B radiation--.

On column 6, line 37 "Bradiation" should be --B radiation--.

UNITED STATES PATENT AND TRADEMARK OFFICE
CERTIFICATE OF CORRECTION

PATENT NO. : 5,025,154

DATED : June 18, 1991

INVENTOR(S) : Risto Ritala et al

It is certified that error appears in the above-identified patent and that said Letters Patent is hereby corrected as shown below:

Column 3, line 48 "absorbator should be --absorber--.

Signed and Sealed this

Twenty-ninth Day of December, 1992

Attest:

DOUGLAS B. COMER

Attesting Officer     Acting Commissioner of Patents and Trademarks